(12) United States Patent
Reuter et al.

(10) Patent No.: US 6,380,135 B1
(45) Date of Patent: Apr. 30, 2002

(54) AGROCHEMICAL COMPOSITIONS

(75) Inventors: Karl Reuter, Freiburg; Christian Krueger, Grenzach-Wyhlen, both of (DE)

(73) Assignee: Syngenta Crop Protection, Inc., Greensboro, NC (US)

( * ) Notice: Subject to any disclaimer, the term of this patent is extended or adjusted under 35 U.S.C. 154(b) by 0 days.

(21) Appl. No.: 09/254,217

(22) PCT Filed: Sep. 2, 1997

(86) PCT No.: PCT/EP97/04783

§ 371 Date: Mar. 3, 1999

§ 102(e) Date: Mar. 3, 1999

(87) PCT Pub. No.: WO98/09516

PCT Pub. Date: Mar. 12, 1998

(30) Foreign Application Priority Data

Sep. 3, 1996 (DE) .......................................... 196 35 631

(51) Int. Cl.$^7$ .............................................. A01N 25/14
(52) U.S. Cl. ........................ 504/366; 504/367; 514/944; 514/951; 514/952
(58) Field of Search ................................. 504/366, 367; 514/944, 951, 952

(56) References Cited

U.S. PATENT DOCUMENTS

| 5,230,892 A | | 7/1993 | Feyen et al. ................. 424/409 |
| 5,294,594 A | * | 3/1994 | Kimler et al. ............... 504/116 |
| 5,476,833 A | | 12/1995 | Fersch et al. ................ 504/116 |

FOREIGN PATENT DOCUMENTS

| CH | 421158 | | 3/1967 |
| EP | 473003 | | 1/1901 |
| EP | 0 501 798 | * | 9/1992 |

* cited by examiner

Primary Examiner—S. Mark Clardy
(74) Attorney, Agent, or Firm—William A. Teoli, Jr.

(57) ABSTRACT

Agrochemical granulated material which is dispersible in water and contains a mixture that is liquid, gel-like, or waxy at +25° C., comprising at least one agrochemical active ingredient and at least one surface-active compound and a thickening agent, and optionally having an outer coating, characterized in that the granulated material has plastic behavior at +25° C.

10 Claims, 1 Drawing Sheet

AGROCHEMICAL COMPOSITIONS

This application is a 371 of PCT/E197/04783 filed Sep. 2, 1997.

The present invention relates to a new type of agrochemical granulated material, which is dispersible in water so as to produce a spray liquor that is ready for use.

Commercial forms of agrochemical active ingredients, that are dispersible in water, are conventional in practice. As well as liquid forms such as emulsion concentrates or suspension concentrates, solid forms such as granules that are dispersible in water, exist commercially. The chosen commercial formulation is basically determined by the physical parameters of the selected active ingredients and admixtures such as surfactants, emulsifiers or carriers. For example, for liquid active ingredients and admixtures, normally liquid commercial forms are chosen, and for solid ones the solid forms of preparation are chosen. In the case of liquid active ingredients, the liquid forms of preparation can normally contain higher concentrations of the active ingredient than the solid forms, but require stable transport containers such as canisters or casks, the return transport and cleaning or disposal of which after emptying give rise to additional costs. On the other hand, the solid forms of preparation may be transported in plastic bags or paper sacks, which can be easily folded up and disposed of after emptying, without giving rise to significant costs. The known solid commercial forms may also be selected for liquid active ingredients or liquid admixtures, if a high proportion of solid, absorbent carrier material is chosen. The proportion of liquid components consisting of active ingredient and admixtures in these dispersible, adsorbed, granulated materials may not in general exceed 20 to 25 percent by weight.

In agricultural practice, there is therefore a need for solid commercial forms, especially granular forms, which allow high proportions of liquid and waxy components such as active ingredients and admixtures to be incorporated therein.

In accordance with the invention, an agrochemical granulated material is prepared, which is dispersible in water and contains a mixture, that is liquid, gel-like or waxy at +25° C., comprising at least one agrochemical active ingredient and at least one surface-active compound and a thickening agent. It optionally has an outer coating and is characterised in that the granulated material has plastic behaviour at 25° C. These new type of granulated materials may contain up to 90% of liquid, gel-like or waxy constituents. The proportion of these constituents is in general preferably 40 to 90%.

An agrochemical granulated material which is dispersible in water, in terms of this application, is understood to be a granular composition for agrochemical active ingredients, which is present as granulated material in its commercial, transport and storage form, and which when preparing an aqueous dispersion breaks down in water automatically or with light stirring, to form a homogeneous, sprayable dispersion. At normal ambient temperature, these granulated materials exist as a coarse-grained, free-flowing, non-sticking or non-drying granulated material. Normally, the granulated materials according to the invention are dust-free.

Compared with the previously known dispersible granulated materials, which as such contain liquid contents such as active ingredients of surface-active compounds or liquid mixtures thereof, the granulated materials according to the invention are superior in that they only contain small proportions of solid carrier materials, that is, the granulatable raw material is not produced by adsorption of the liquid components on the solid inert carrier material. The maximum charge of granulated materials consisting of adsorptive carrier materials for liquid constituents is 20 to 25% according to present experience. In contrast, the granulated material according to the invention is a surfactant/matrix granulated material or an active ingredient/matrix granulated material, in which the agrochemical active ingredient is embedded in a matrix consisting of a surface-active material (surfactant), or the surfactant is embedded in a matrix consisting of an active ingredient. In the granulated materials according to the invention, these active ingredient/surfactant mixtures themselves have an aggregate state which is liquid, gel-like or waxy at +25° C., and does not allow granular materials to be formed directly. In accordance with the invention, a granulated material with plastic behaviour is produced from such a mixture, whereby the agrochemical active ingredient is mixed with the surface-active compound to form a homogeneous mixture or dispersion, and this mixture is brought to a granulatable state by adding a small amount of an appropriate thickening agent, this mixture is granulated and the surface of the granulated material obtained is coated if required. This coating may serve to improve the fluidity of the granulated material.

Figure 1:
FIG. 1 shows that no fragments or powdery particles form during the compression process.

Appropriate granulating processes are all conventional processes described in granulating technology, for example spray drying, fluidised bed granulation and in particular extrusion granulation.

The granulated materials obtained by the granulation process according to the invention are normally not sticky at room temperature (+25° C.) and do not dry out even when storing for long periods.

The granulated materials according to the invention are dispersed by stirring into water in the spray tank, to form a dispersion which is ready for use within 5 to 10 minutes.

In contrast to the known adsorbed granulated materials, the granulated materials according to the invention have a plastic consistency (exhibit plastic behavior), that is, under mechanical pressure the grains do not break down into powder or granule fragments, but are basically deformed into flat circular discs. In this way, a cylindrical or spherical grain according to the invention with a diameter of 0.6–2 mm is deformed homogeneously, like a plastic, to form an elliptic or circular plate at a thickness of at most 20% of its original diameter, when compressed between two non-plastic parallel plates.

Suitable thickening agents in the granulated materials according to the invention may be all substances which are able to thicken the liquid, gel-like or waxy mixtures of agrochemical active ingredients and surface-active substances, in such a way that the admixed mass has a consistency suitable for granulation. To this end, the following are especially suitable: ultra-fine silicon dioxide, pyrogenic silicon dioxide or precipitated silicon dioxide; ultra-fine aluminium silicates such as bentonite, organic polymers such as polyvinyl alcohol derivatives, cellulose derivatives, polysaccharide derivatives or ultra-fine urea- or melamine/formaldehyde-condensates. By ultra-fine forms of the thickening agents are understood powder forms with grain sizes of between 0.01 μm and 10 μm. Commercially available thickening agents, which may be used in the granulated materials according to the invention, are for example AEROSIL (DEGUSSA AG, Frankfurt, Germany); CELITE (MANVILLE, Denver, USA); PERGOPAK (MARTINSWERK, Bergheim, Germany); ARGIREC (BLANCS MINEREAUX de PARIS, Paris, France).

A particular advantage of the granulated materials according to the invention is their high content of liquid, gel-like or waxy mixture, which preferably makes up between 40 and 90% of the total weight of the granulated material.

If desired, the granulated materials according to the invention may contain, in addition to the active ingredients and surface-active substances, further carriers and admixtures that are usual in agriculture. Preferably, the content of carriers is at most up to 55% of the total weight. In particular, the proportion of carriers is less than 10% of the total weight.

The proportion of thickening agent in the granulated materials according to the invention is generally up to 20 percent by weight, preferably 5 to 20, especially 5 to 10 percent by weight.

The granulated materials according to the invention preferably contain 40 to 90% of the liquid, gel-like or waxy mixture comprising agrochemical active ingredient and surface-active compound, 5 to 20% of a thickening agent, and a carrier and/or admixture which is usual in agriculture.

Carriers that are usual in agriculture, in the terms of the present invention, are materials which are acceptable in agriculture and are added to the active component to bring it into a form which is easier or better to use, or to bring it to a useful or desirable strength of activity. This may be for example talc, kaolin or diatomaceous earth.

The liquid, gel-like or waxy mixture incorporated in the granulated material according to the invention consists either of a liquid or solid agrochemical active ingredient and a liquid surface-active compound, or of a liquid active ingredient and a liquid or solid surface-active compound.

The agrochemical active ingredients may be fertilizers, growth regulators and pesticides. The granulated materials are preferably used as a formulation for pesticides having acaricide, fungicide, herbicide or insecticide activity.

For example, the following active ingredients may be granulated by the formulation technique according to the invention:

Acaricides and insecticides such as benthiocarb, diflubenzuron, teflubenzuron, lufenuron, diafenthiuron or pyrethroide such as bifenthrin, bioallethrin, tau-fluvalinate, resmethrin, permethrin, cypermethrin, cyfluthrin, cyhalothrin, deltamethrin, tefluthrin or tetramethrin, furtheron pymetrozin, thiocyclam, fenoxycarb, methopren, abamectin and emamectin.

Preference is given to lufenuron, diafenthiuron, tau-fluvalinate and cypermethrin.

Fungicides such as benomyl, carbendazim, cyprodinil, chlorthalonil, dimethomorph, edifenphos, fenpropimorph, metalaxyl, (R)-metalaxyl (enantiomer), oxadixyl, pyrifenox, thiabendazol, tridemorph, azoxystrobin, kresoxim-methyl or triazoles such as propiconazol, difenoconazol, bromoconazol, cyproconazole, epoxyconazol, hexaconazol, ipconazol, fenbuconazol, myclobutanil, penconazol, tebuconazol, triadimefon, triadimenol, tetraconazol, triticonazol, or uniconazol; furtheron acibenzolar-S-methyl, famoxadone, quinoxyfen, spiroxamin, fludioxonil, fenpiclonil, fenhexamid and 2-[α-{[(α-methyl-3-trifluoromethyl-benzyl)imino]-oxy}-o-tolyl]-glyoxylic acid-methylester-O-methyloxim. Preference is given to carbendazim, cyprodinil, chlorthalonil, metala,yl, (R)-metalaxyl, oxadixyl, azoxystrobin, kresoxim-methyl, propiconazol, cyproconazole, epoxyconazol and tebuconazol.

Herbicides such as chlortoluron, bifenox, bromoxynil and its octanoate, ioxynil and its octanoate, fluometuron, glufosinate, glyphosate, pendimetalin, sulcotrione, 3-phenyl-4-hydroxy-6-chlorpyridazine, alachlor, dimethenamide, metolachlor, (S)-metolachlor (enantiomer), or sulfonyl-ureas such as bensulfuron, primisulfuron, prosulfuron, triasulfuron, pyrazosulfuron, nicosulfuron, rimsulfuron, thifensulfuron, triflusulfuron, oxasulfuron, cinosulfuron; furtheron atrazine, propaquizafop, trinexapac-ethyl, pyridate, dicamba, clodinafop, fenclorin. Preference is given to fluometuron, glufosinate, glyphosate, sulcotrione, 3-phenyl-4-hydroxy-6-chlorpyridazin, dimethenamid, metolachlor, (S)-metolachlor, triasulfuron, nicosulfuron or rimsulfuron.

The components in the mixture may be solid or liquid, surface-active substances. These surface-active substances are preferably anionic surfactants from the series of fat alcohol ether sulphonates, such as lauryl ether sulphates, sulphosuccinates, sulphonated naphthalene/formaldehyde condensates and alkylaryl sulphonates, or non-ionic surfactants from the series of alkylphenol ethoxylates, such as nonylphenol ethoxylates, fat alcohol ethoxylates such as oleyl alcohol ethoxylates or lauryl alcohol ethoxylates, fat amine ethoxylates and mixtures thereof, ethoxylated oils such as ethoxylated castor oil and rapeseed oil, ethoxylated fatty acid methyl esters, sorbitan esters and ethoxylated sorbitan esters, alkyl- and alkylaryl-polyethylene oxide phosphoric acid esters, ethoxylated polyethylene glycols, ethylene oxide/propylene oxide adducts, alkyl-succinic acid anhydride condensates, fatty acid amide ethoxylates, alkyl-polyglycosides or silicone surfactants.

Examples of commercial types of surfactant that may be formulated into granulated materials according to the invention are:
GENAPOL (HOECHST AG, Frankfurt, Germany); laurylether sulphate (HOECHST AG, Frankfurt, Germany); SYNPERONIC (ICI EUROPE LTD, Kortenberg, Belgium), ARMOBLEN (AKZO NOBEL SURFACE CHEMISTRY BV, Amerstoort, Netherlands), BEROL (AKZO NOBEL SURFACE CHEMISTRY BV, Amersfoort, Netherlands), CROVOL (CRODA OLEOCHEMICALS, North Humberside, Great Britain), ALKAMULS (RHONE POULENC, Paris, France), oleic acid methylester (HUELS AG, Marl, Germany), AEROSOL (CYTEC INDUSTRIES INC., West Peterson, N.J., USA), CRILL and CRILLET (CRODA OLEOCHEMICALS, North Humberside, Great Britain), CRODAFOS (CRODA OLEOCHEMICALS, North Humberside, Great Britain),SOPROPHOR (RHONE-POULENC, Paris, France), ATLOX (ICI EUROPE LTD, Kortenberg, Belgium), MARLOX (HUELS AG, Marl, Germany), ASAC (ICI EUROPE LTD, Kortenberg, Belgium), GENAGEN (HOECHST AG, Frankfurt, Germany); AG 6202 (AKZO NOBEL SURFACE CHEMISTRY BV, Amersfoort, Netherlands), SUPRAGIL (RHONE POULENC, Paris, France), calcium dodecylbenzene-sulphonate (HOECHST AG, Frankfurt, Germany);.SILWET (OSI SPECIALTTIES, Tarrytown, N.Y., USA).

If necessary, in addition to these surface-active substances, the granulates may also contain further additives, for example anti-foaming agents.

The granulated materials according to the invention are normally non-sticking or non-drying, and exist as free-flowing granular form. If it is desired that the surface of the granulated materials according to the invention are further treated against adhesion, this surface may be covered with one of the said powdery carriers such as kaolin or talc. This coating may take place for example by dusting with kaolin or talc, or by rolling in a mixing or drying drum covered with kaolin or talc. Alternatively, the surface of the granulate may also be coated e.g. with a water-soluble polymer film of polyvinyl alcohol or polyvinyl pyrrolidone in a film-forming drum. The granulated materials according to the invention enable not only a high concentration of liquid active ingredients to be obtained, but also a high concentration of liquid, gel-like or waxy surface-active substances. In a typical granular formulation according to the invention, there is for example 10–30% active ingredient, 40–70% surface-active substance, 10–20% thickening agent and 0–10% powdery carriers. Compositions such as 24% active ingredient, 50% surface-active substance, and 26% thickener, dispersing agents, wetting agents and carriers; or 25% active ingredient, 60% surface-active substance, 10% thickening agent, 1.5% defoamer and 2.5% kaolin may be mentioned by way of example.

The following examples serve to illustrate the invention, but in no way restrict it.

EXAMPLE 1

Cyproconazole Granulated Materials

56% lauryl ether sulphate (dry content) in the form of a 70% water-containing paste (Genapol® LRO, Hoechst AG, Frankfurt) is mixed to a homogeneous dispersion with 1.5% defoamer (Fluowet® PL 80, Hoechst AG, Frankfurt), 25% cyproconazole (technical, 96%) and 10% thickening agent (Aerosil®200, Degussa, Frankfurt). The paste obtained is extruded in an extrusion press having a perforated screen of 0.5–2.0 mm hole diameter. The extruded cord-like material is divided into cylindrical grains of 2 to 20 mm length and the surface thereof is coated with 4.5% powdery kaolin (Tuboryl® N, SILICE et KAOLIN, Paris, France). The extruded granulated material is dried in a drying appliance up a residual moisture of ca. 3% water content. During the drying process, the granulated material hardens further. The granulated material obtained contains 24% pure cyproconazole, 56% GENAPOL LRO, 10% AEROSIL, 4,50% TUBORYL N, 1,50% FLUOWET PL 80, and ca. 3% water.

EXAMPLE 2

Further Granulated Materials

The following plastic granulated materials are produced analogously to the process in example 1:

Details in percent by weight
Residual moisture of the granulated material: 1–5% water

| Component | 2a | 2b | 2c | 2d | 2e | 2f | 2g | 2h |
|---|---|---|---|---|---|---|---|---|
| cyproconazole | 25 | 25 | 25 | 25 | | | | 30 |
| Tau-fluvalinate | | | | | 20 | 25 | 15 | |
| GENAPOL 0–80 | | | | 40 | | 40 | | 55 |
| Laurylether sulphate | 55 | 40 | 40 | | 60 | | 57 | |
| AEROSIL 200 | 12 | | | | 10 | | | 10 |
| CELITE 209 | | | 18 | | | | 10 | |
| PERGOPAK | | 15 | 8 | 16 | | 16 | 10 | |
| AGRIREC B24 | 4 | 10 | | 10 | 6 | 10 | | |
| SUPRAGIL El21O | | 6 | 5 | 7 | | 7 | 2 | 1 |
| kaolin (TUBORYL N) | | | | | | | | 3 |

EXAMPLE 3

Plasticity Test

Figure 2:
FIG. 2 in contrast, shows that small fragments form when compressing a non-plastic granulated material.

A cylindrical grain (obtained according to example 1) of 1 mm diameter and 4 mm length is positioned lengthways between two glass plates. The glass plates are compressed with even pressure until 0.15 mm apart. During the compression process, the grain becomes deformed into a circular or elliptic homogeneous plate of 0.15 mm height. During the compression process, no fragments or powdery particles (FIG. 1) are formed. In contrast to this, when compressing a non-plastic granulated material, for example an adsorbed granulated material, small fragments (FIG. 2) are obtained.

In various plasticity tests with longer cylindrical grains (10 mm length, 1 mm diameter), the deformed elements obtained were almost square-shaped : at a final height of 0.2 mm, the width was 6–8 mm and the length 11–17 mm.

EXAMPLE 4

Biological Test

In a field test in Switzerland, the effects of cyproconazole in various types of formulation on Erisyphe graminis (powdery mildew) were determined in barley.

Field plots (2 m×7.5 m) were sown on 25th August with barley seed of the cultivar "Golden Promise". After emergence, the plots were sprayed on 18th September with spray liquors produced from the different formulations. The amounts applied were respectively 80 g cyproconazole per hectare. Evaluation was effected 17 days and 24 days after treatment and compared with untreated comparison plots, and the results given as percentage control of the powdery mildew attack (100%=no attack; 0% as untreated control).

The following formulations were tested:

| | |
|---|---|
| Composition 1 | (cyproconazole, 25% wettable granulated material according to the present invention: 25% cyproconazole, 51% lauryl ether sulphate, 10% AEROSIL 200, 6% TUBORYL N, 4% silicone defoamer, 4% water). |
| ALTO 100 SL | (cyproconazole, 10% solution concentrate, commercial form: 10% cyproconazole, 8.5% N-methylpyrrolidone, 5% AGRILAN F 546 (HARCROS CHEM., Great Britain), 76.5% polyethylene glycol). |
| SENTINEL 40 WG | (cyproconazole, 40% wettable granulated material based on solids: 43.96% technical (91%) cyproconazole, 20% ULTRAZIN NA (LIGNOTECH, Norway), 36.04% MIKRODOL EXTRA (NORWEGIAN TALC, Norway)). |

Test Results

Cyproconazole, in barley "Golden Promise" against powdery mildew (*Erisyphe graminis*) 80 g cyproconazole per hectare percentage control 17 DAT, 24 DAT

| Formulation | 17 DAT | 24 DAT |
|---|---|---|
| composition 1 | 87 | 76 |
| ALTO 100 SL | 80 | 68 |
| SENTINEL 40 WG | 62 | 35 |

For a single application of 80 g active ingredient per hectare, the granular formulation according to the invention had the best effect, which clearly surpassed the effect of the liquid commercial form ALTO SL. The effect of the granular commercial form SENTINEL WG was considerably weaker in this test.

What is claimed is:

1. An agrochemical granulated material, which is dispersible in water and contains a mixture, that is liquid, gel, or waxy at +25° C. comprising at least one agrochemical active ingredient and at least one surface-active compound and additionally a thickening agent, characterized in that the liquid, gel or waxy mixture consists of a liquid or solid agrochemical active ingredient and a liquid surface-active compound, or of a liquid active ingredient and a liquid or solid surface-active compound, and further characterized in that the granulated material has plastic behavior at +25° C.

2. The granulated material of claim 1, characterized in that a cylindrical or spherical grain with a diameter of 0.6 to 2 mm is deformed homogeneously to form an elliptic or circular plate at a thickness of at most 20% of its original diameter when compressed between two non-plastic parallel plates.

3. The granulated material of claim 1, characterized in that the content of liquid, gel, or waxy mixture in said granulated material is 40 to 90% of its total weight.

4. The granulated material of claim 1, characterized in that it contains up to 20% by weight of a thickening agent.

5. The granulated material of claim 1, characterized in that the agrochemical active ingredient is a pesticide having acaricide, fungicide, herbicide, or insecticide activity.

6. The granulated material of claim 5, characterized in that the herbicide is selected from the group consisting of fluometuron, glufosinate, glyphosate, sulcotrione, 3-phenyl-4-hydroxy-6-chlorpyridazine, dimethenamide, metolachlor, (S)-metolachlor, triasulfuron, nicosulfuron, and rimsulfuron.

7. The granulated material of claim 5, characterized in that the fungicide is selected from the group consisting of carbendazim, cyprodinil, chlorthalonil, metalaxyl, (R)-metalaxyl, oxadixyl, azoxystrobin, kresoxim-methyl, propiconazol, cyproconazole, epoxyconazol, and tebuconazol.

8. The granulated material of claim 5, characterized in that the acaricide or insecticide is selected from the group consisting of lufenuron, diafenthiuron, tau-fluvalinate, and cypermnethrin.

9. The granulated material of claim 1, characterized in that the surface active compound is (a) an anionic surfactant selected from the group consisting of fatty alcohol ether sulphonates, sulphosuccinates, alkyl- and alkylaryl-polyethylene oxide phosphoric acid esters, sulphonated naphthalene/formaldehyde condensates, and alkylarylsulphonates; or (b) a non-ionic surfactant selected from the group consisting of alkylphenolethoxylates, fatty alcohol ethoxylates, fatty amine ethoxylates and mixtures thereof, ethoxylated fatty acid methyl ester, sorbitan esters and ethoxylated sorbitan esters, ethoxylated polyethylene glycols, ethylene oxide/propylene oxide adducts, alkyl-succinic acid anhydride condensates, fatty acid amide ethoxylates, alkyl polyglycosides, and silicone surfactants.

10. A process for the production of a granulated material according to claim 1, characterized in that the agrochemical active ingredient is mixed with the surface-active compound to form a homogeneous first mixture, and this first mixture is brought to a granulatable state by adding a thickening agent to form a second mixture, and said second mixture is granulated, and the surface of the resulting granulate is optionally coated.

* * * * *